(12) United States Patent
Mueller et al.

(10) Patent No.: US 11,135,065 B2
(45) Date of Patent: Oct. 5, 2021

(54) 3-D PRINTED ORTHOPEDIC IMPLANTS

(71) Applicant: Life Spine, Inc., Huntley, IL (US)

(72) Inventors: Richard M. Mueller, St. Charles, IL (US); Eugene Shoshtaev, Del Mar, CA (US); Gregory Palagi, Geneva, IL (US); Daniel P. Predick, West Lafayette, IN (US); Michael S. Butler, St. Charles, IL (US)

(73) Assignee: LIFE SPINE, INC., Huntley, IL (US)

( * ) Notice: Subject to any disclaimer, the term of this patent is extended or adjusted under 35 U.S.C. 154(b) by 0 days.

(21) Appl. No.: 15/916,765

(22) Filed: Mar. 9, 2018

(65) Prior Publication Data

US 2018/0256336 A1 Sep. 13, 2018

Related U.S. Application Data

(60) Provisional application No. 62/469,822, filed on Mar. 10, 2017, provisional application No. 62/576,975, filed on Oct. 25, 2017.

(51) Int. Cl.
*A61F 2/44* (2006.01)
*A61F 2/30* (2006.01)
(Continued)

(52) U.S. Cl.
CPC .............. *A61F 2/30* (2013.01); *A61F 2/2846* (2013.01); *A61F 2/447* (2013.01); *A61F 2/4455* (2013.01);
(Continued)

(58) Field of Classification Search
CPC ............ A61F 2/4455; A61F 2002/4475; A61F 2/30767; A61F 2002/30769;
(Continued)

(56) References Cited

U.S. PATENT DOCUMENTS

| 8,430,930 B2 * | 4/2013 | Hunt .................. A61B 17/1604 |
| | | 623/17.11 |
| 2008/0161927 A1 | 7/2008 | Savage et al. |

(Continued)

FOREIGN PATENT DOCUMENTS

| EP | 1 961 433 A1 | 8/2008 |
| EP | 3 045 151 A1 | 7/2016 |

(Continued)

OTHER PUBLICATIONS

International Preliminary Report on Patentability for PCT/US2018/021783, dated Sep. 19, 2019, 10 pages.

(Continued)

*Primary Examiner* — Eduardo C Robert
*Assistant Examiner* — Christina Negrellirodriguez
(74) *Attorney, Agent, or Firm* — Foley & Lardner LLP

(57) ABSTRACT

A spinal interbody implant is fabricated using 3-D printing to provide an engineered structure of one or more porous, permeable, or non-solid portions with or without one or more solid, dense, or micro-dense portions. The porous, permeable, or non-solid structure can be a mesh, lattice, web, weave, honeycomb, simple cubic, tetrahedral, diamond, or otherwise with the number and size of its pores, holes, perforations, or openings, as well as the distance or thickness between them, can vary accordingly. Some portions of the porous, permeable, or non-solid structure(s) may have porosities and/or thicknesses different than other portions. The solid, dense, or micro-dense structure may be constant throughout the body of the implant or may be a range of densities throughout the body of the implant.

(Continued)

Alternately, one or more portions of the implant may have a range of densities throughout its body ranging from solid to a maximum porosity.

18 Claims, 17 Drawing Sheets

(51) Int. Cl.
    *A61F 2/28*     (2006.01)
    *B33Y 80/00*     (2015.01)
    *B33Y 70/00*     (2020.01)

(52) U.S. Cl.
    CPC ............... *B33Y 70/00* (2014.12); *B33Y 80/00* (2014.12); *A61F 2002/2817* (2013.01); *A61F 2002/2835* (2013.01); *A61F 2002/30011* (2013.01); *A61F 2002/3092* (2013.01); *A61F 2002/3093* (2013.01); *A61F 2002/30593* (2013.01); *A61F 2002/30622* (2013.01); *A61F 2002/30677* (2013.01); *A61F 2002/30769* (2013.01); *A61F 2002/30784* (2013.01); *A61F 2002/30962* (2013.01); *A61F 2002/30985* (2013.01); *A61F 2002/4495* (2013.01); *A61F 2310/00017* (2013.01); *A61F 2310/00023* (2013.01)

(58) Field of Classification Search
    CPC ........ A61F 2002/30772; A61F 2/30907; A61F 2002/3092; A61F 2002/3093; A61F 2/446; A61F 2/4465; A61F 2/447; A61F 2002/30143; A61F 2002/30146; A61F 2/44; A61F 2/442; A61F 2/46

USPC ........................................... 623/17.11, 17.16
See application file for complete search history.

(56) References Cited

U.S. PATENT DOCUMENTS

| | | | |
|---|---|---|---|
| 2011/0137418 A1* | 6/2011 | O'Neil | A61F 2/28 623/16.11 |
| 2012/0078315 A1* | 3/2012 | Sweeney | A61F 2/442 606/86 A |
| 2013/0116793 A1* | 5/2013 | Kloss | A61F 2/442 623/17.16 |
| 2014/0107786 A1 | 4/2014 | Geisler et al. | |
| 2014/0236299 A1* | 8/2014 | Roeder | A61F 2/28 623/17.16 |
| 2015/0148907 A1* | 5/2015 | Kleiner | A61B 17/8822 623/17.16 |
| 2015/0238324 A1* | 8/2015 | Nebosky | A61F 2/4465 623/17.16 |
| 2016/0270920 A1 | 9/2016 | Dawson et al. | |
| 2016/0324656 A1* | 11/2016 | Morris | A61F 2/4455 |

FOREIGN PATENT DOCUMENTS

| | | |
|---|---|---|
| EP | 3 050 540 A1 | 8/2016 |
| WO | WO-2016/130878 A1 | 8/2016 |

OTHER PUBLICATIONS

International Search Report for PCT/US2018/021783, dated Jun. 7, 2018, 5 pages.

\* cited by examiner

3-D PRINTED ORTHOPEDIC IMPLANTS

CROSS-REFERENCE TO RELATED APPLICATIONS

This U.S. non-provisional patent application claims the benefit of and/or priority under 35 U.S.C. § 119(e) to U.S. provisional patent application Ser. No. 62/469,822 filed Mar. 10, 2017 titled "3-D Printed Orthopedic Implants," and U.S. provisional patent application Ser. No. 62/576,975 filed Oct. 25, 2017 titled "3-D Printed Orthopedic Implant," the entire contents of both of which are specifically incorporated herein by reference.

FIELD OF THE INVENTION

The present invention relates to orthopedic implants and, more particularly, to fabrication of orthopedic implants using 3-D printing.

BACKGROUND OF THE INVENTION

Many people contend with orthopedic issues as a result of age, disease, and trauma, as well as congenital and acquired complications and conditions. While some of these issues can be alleviated without surgery, other issues respond better to surgery. In some cases, surgery may include the insertion of an orthopedic implant.

There are various orthopedic implants for various skeletal issues. Without being exhaustive, orthopedic implants have been made for the hand, shoulder, foot, knee, spine, and ankle. One area where orthopedic implants are frequently used is in or relative to the spine. Orthopedic spine implants such as rods, vertebral body replacements (interbody or fusion cages), vertebral intrabody devices, screws, and the like are now in common use. For instance, if vertebral fusion is required, a spine implant known as an interbody cage typically along with bone graft or bone graft material may be used.

An interbody cage is a device that is placed in the disc space between adjacent vertebrae of a recipient's spine. The interbody cage includes openings, bores, and/or the like to permit the introduction and/or carrying of bone graft/bone graft material in order to allow the bone graft/bone graft material to grow from one vertebra through the interbody cage and to the adjacent vertebra. Such interbody cages provide excellent fixation such that most recipients do not require additional implants such as plates and/or bone screws.

There are several reasons for and approaches to implanting an interbody cage in a patient's spine, as well as styles of interbody cages. The surgical approach may influence interbody cage design, for instance, the direction of insertion of the interbody cage. Typical surgical approaches are known as and include TLIF, PLIF, Lateral, ALIF, and others, for both expandable interbody cages and fixed height interbody cages.

For various reasons, it would be desirable to have a custom or unique orthopedic implant for a particular individual, for instance a spine implant that is made for the particular anatomy of the individual. It would also be desirable to provide an "on the spot" orthopedic implant of any type for surgical use. It would be further desirable to provide a 3-D printed orthopedic implant such as, but not limited to, a spine implant or device of any type. Other desires are many but not herein enumerated.

In view of the above, it is one object of the present invention to provide a custom or unique orthopedic implant, such as a spinal interbody device of any type for implanting in a spine. It is also an object of the present invention to provide an "on the spot" orthopedic implant of any kind, such as, but not limited to, a spinal interbody device. It is further an object to provide 3-D printing of orthopedic implants with integral bone growth structure(s) or structuring that promote bony ingrowth. Other objects are contemplated but not herein enumerated.

SUMMARY OF THE INVENTION

A spinal interbody implant is fabricated using 3-D printing (with or without modeling individual pathology via modeling technology such as, but not limited to, computed tomography (CT)) to provide an engineered structure of one or more porous, permeable, or non-solid portions with or without one or more solid, dense, or micro-dense portions. The porous, permeable, or non-solid structure can be a mesh, lattice, web, weave, honeycomb, simple cubic, tetrahedral, diamond, or otherwise with the number and size of its pores, holes, perforations, or openings, as well as the distance or thickness between them, can vary accordingly. Some portions of the porous, permeable, or non-solid structure(s) may have porosities and/or thicknesses different than other portions. The solid, dense, or micro-dense structure may be constant throughout the body of the implant or may be a range of densities throughout the body of the implant. Alternately, one or more portions of the implant may have a range of densities throughout its body ranging from solid to a maximum porosity.

The 3-D printed orthopedic implant can be fabricated for any orthopedic application including, but not limited to, spine implants, foot and ankle implants, hand implants, joint implants, bone implants, and the like (collectively, "implants"), as well as for any surgical approach.

In all cases, the implant is characterized by a body having either one or more solid, dense or micro-dense portions and one or more porous, permeable, or non-solid portions, or one or more porous, permeable, or non-solid portions. The porous, permeable, or non-solid structure may be, but not limited to, a mesh, lattice, web, weave, honeycomb structure, simple cubic structure, tetrahedral structure, diamond structure, or the like. The porosity of the non-solid structures can be fabricated as desired such as the number and size of its pores, holes, perforations, or openings as well as distance or thickness between the pores, holes or openings. The overall thickness of the porous structure may also be fabricated as desired. Moreover, some portions of the non-solid structure may have a porosity and/or thickness that is different from other porous portions. The solid, dense, or micro-dense structure may be constant throughout the body of the implant or may be a range of densities throughout the body of the implant. Alternately, one or more portions of the implant may have a range of densities throughout its body ranging from solid to a maximum porosity. The body may be comprised of one or more such structures to provide structural strength and/or any necessary or desired aid in bony in-growth. The non-solid structure helps aid in boney ingrowth.

With respect to implants for the spine, intervertebral (interbody), intravertebral (intrabody), and vertebral body implants may be 3-D printed per the present principles. Shown and described herein are exemplary forms of orthopedic implants fashioned as spinal interbody devices fabricated using 3-D printing per the present principles, the external structure(s) and the internal structure (s) thereof engineered as appropriate for the surgical implanting approach and/or patient pathology.

In one form, a spinal interbody device has a body characterized by a solid or dense exterior geometry or shell as explained above for structural strength and a porous, permeable, or non-solid interior structure as explained above with surfaces that are exposed by and which interface with the cephalad and caudel endplates of the solid or dense exterior shell for promoting fusion between adjacent boney anatomy.

Various spinal interbody devices may be 3-D printed utilizing the principles of the present invention including, but not limited to, general spinal interbody cages, TLIF cages, PLIF cages, Lateral cages, ALIF cages, and the like, including fixed-height and expandable spinal interbody cages. The spinal interbody devices may thus be designed for any surgical approach, including lateral, anterior, and posterior. Changes to the arrangement of the exterior shell with its cutout(s) and/or slot(s), and the non-solid interior that interfaces with the cutout(s) and/or slot(s) provides various spinal interbody devices.

In the case of a solid outer or exterior shell, its structure reinforces its non-solid interior structure. Lateral side slots in the solid exterior walls of the shell need to be a minimum distance from the proximal end (with its insertion features) but distally, the further the slots extend toward the distal end (the bulleted nose or tip) of the spinal interbody implant, the closer the aggregate axial stiffness of the implant will approach the stiffness of the non-solid interior structure (e.g. the lattice structure). In the case where the lateral side slot extends from one lateral side to the other lateral side, wrapping around the nose/tip, making a continuous U-shaped opening, slot, or channel through the solid exterior wall exposing the interior non-solid structure (e.g. lattice). In the case of a T/PLIF implant (such as shown in the Figures) with a continuous opening, slot, or channel (not shown), the anterior (distal) section of the implant will be substantially more compliant than the posterior (proximal) end of the implant, which may result in minimizing subsidence and speeding up fusion.

In view of its design, the posterior (insertion) end of a 3-D printed spinal interbody T/PLIF implant is significantly less likely to subside than the anterior end because of the structure of the endplates with their perimeter being much more densely mineralized than their interior. This means that the posterior/proximal end of the spinal interbody implant can and should be stiffer than the anterior/distal end of the spinal interbody implant.

Through use of 3-D printing principles, materials for and densities and structures of the solid and/or non-solid portions of the implant can be changed based on design criteria such as, but not limited to, surgical approach (e.g. a lateral insertion procedure, a posterior insertion procedure, or an anterior insertion procedure) and pathology.

A method of delivering/injecting bone graft material such as, but not limited to, milled autograph, DBM, cancellous chips, PRP, cellular allograft, and the like (collectively, "bone graft material") into the implant post-implantation through an aperture of the implant is also provided. Delivering/injecting bone draft material post-implantation may be accomplished before or after an introducer instrument has been disengaged from the implant, such introduction/injection of bone graft material, is accomplished through a bore in the introducer instrument.

Further aspects of the present invention will become apparent from consideration of the drawings and the following description of forms of the invention. A person skilled in the art will realize that other forms of the invention are possible and that the details of the invention can be modified in a number of respects without departing from the inventive concept. The following drawings and description are to be regarded as illustrative in nature and not restrictive.

BRIEF DESCRIPTION OF THE DRAWINGS

The present invention will be better understood by reference to the accompanying drawings, wherein.

DETAILED DESCRIPTION OF THE INVENTION

Figure 1:
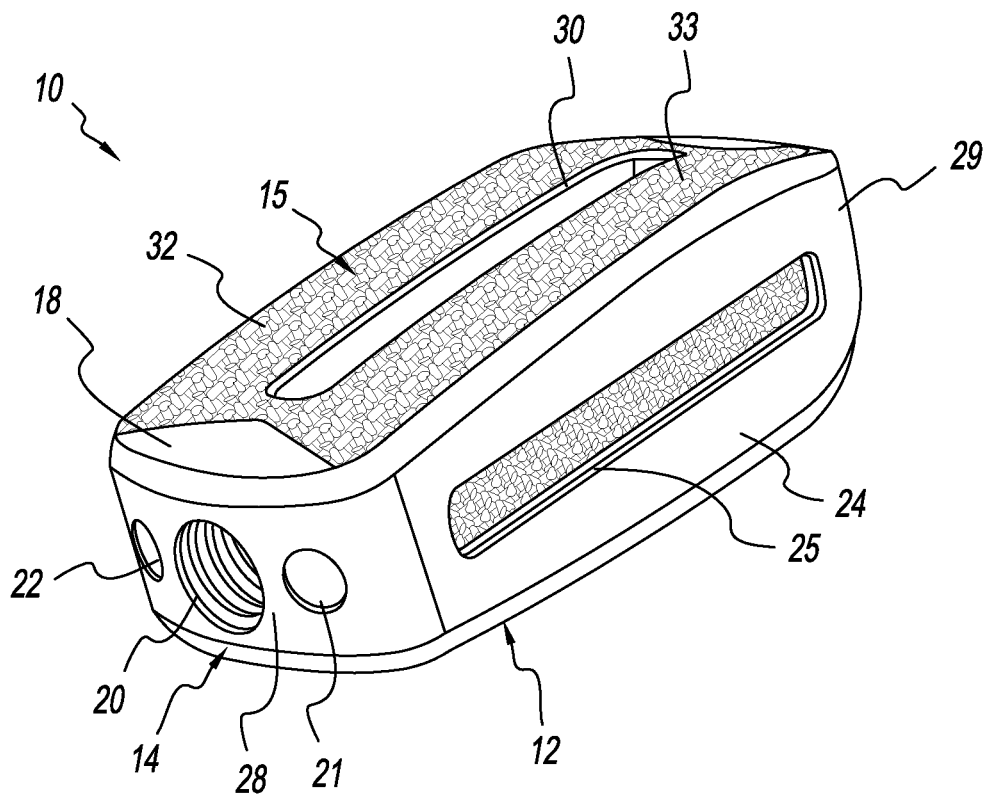
FIG. 1 is an isometric proximal end view of a 3-D printed orthopedic implant fashioned as a spinal interbody implant, particularly designed for posterior intervertebral insertion.
Figure 2:
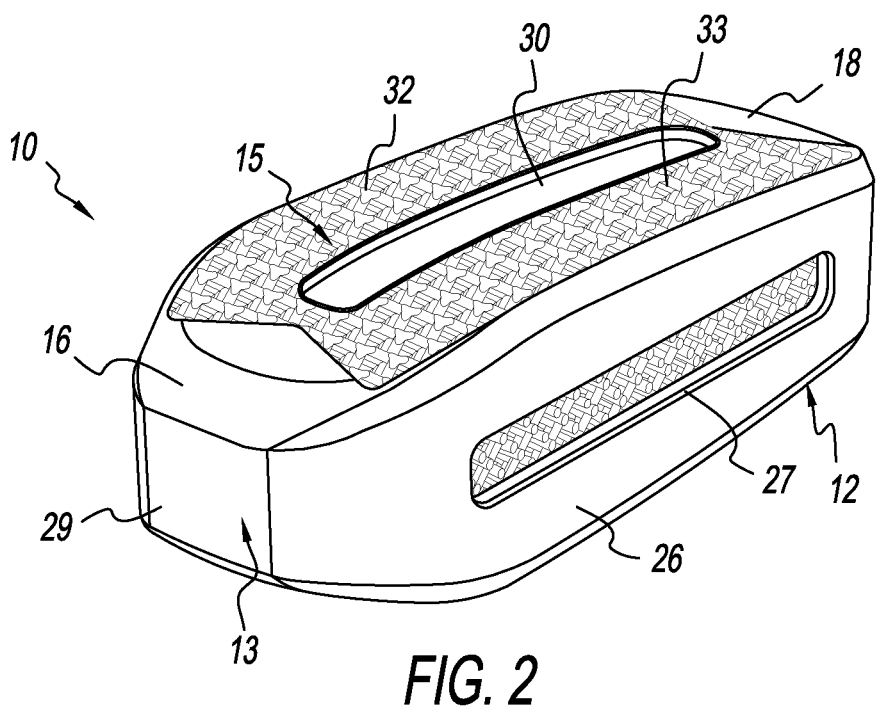
FIG. 2 is an isometric distal end view of the 3-D printed spinal interbody implant of FIG. 1.
Figure 3:
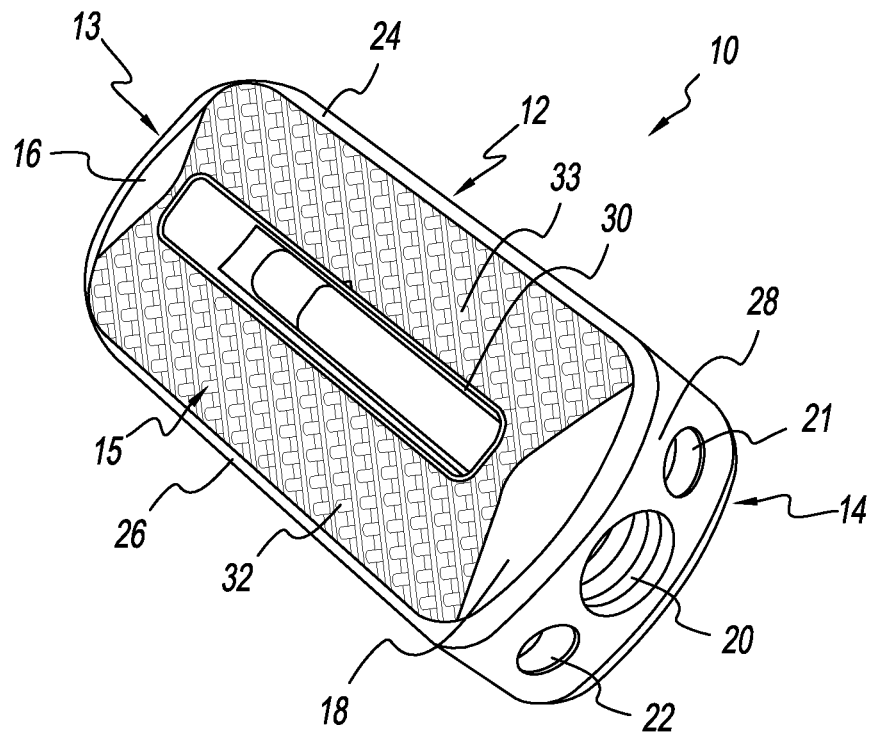
FIG. 3 is an isometric upper proximal end view of the 3-D printed spinal interbody implant of FIG. 1.
Figure 4:
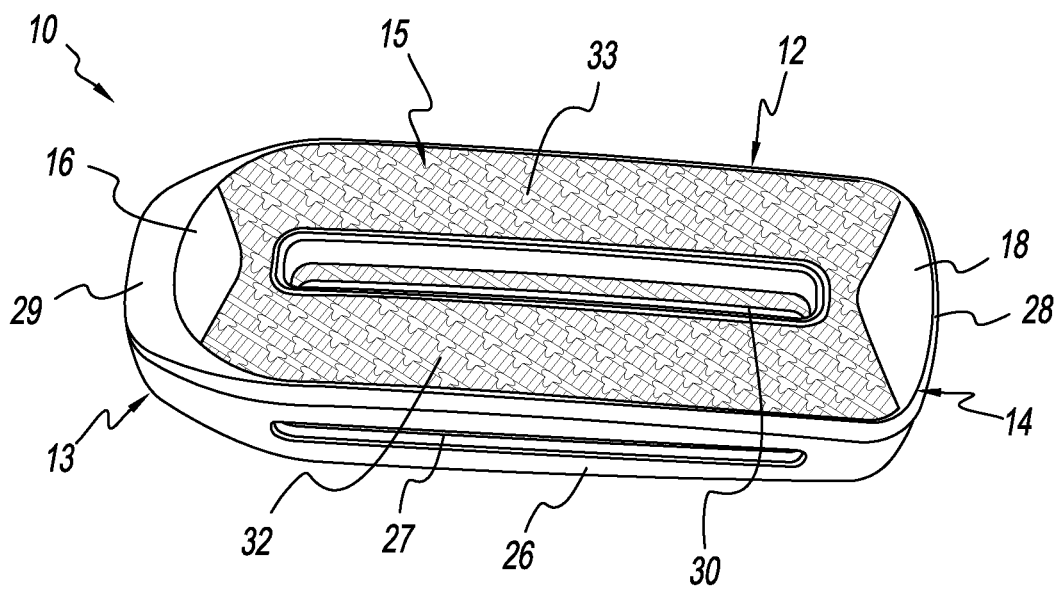
FIG. 4 is an isometric upper lateral side view of the 3-D printed spinal interbody implant of FIG. 1.
Figure 5:
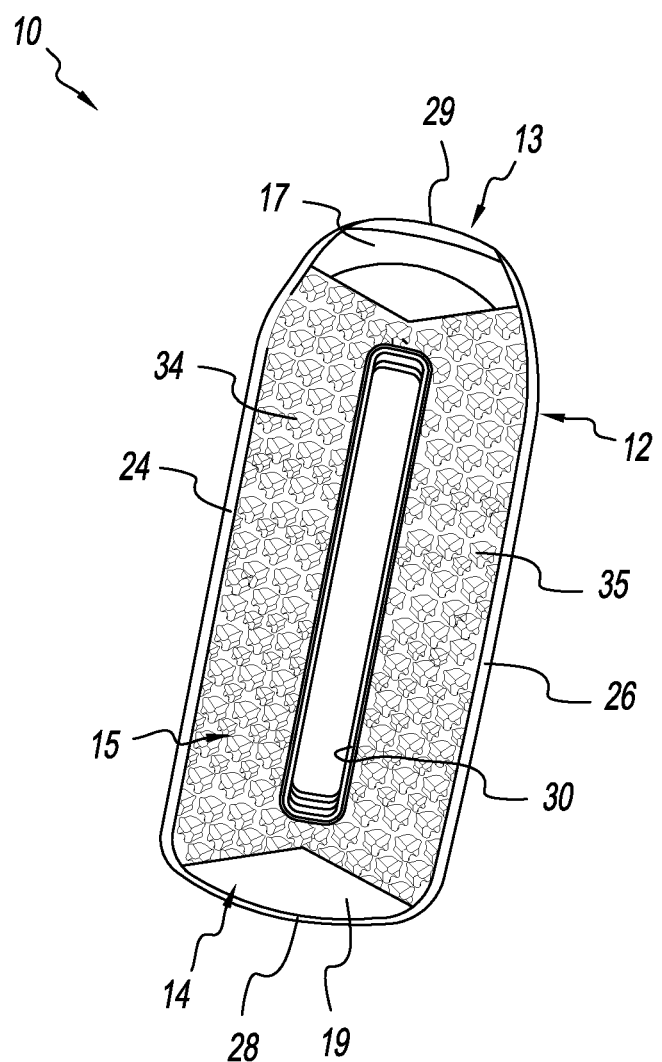
FIG. 5 is a lower plan view of the 3-D printed spinal interbody implant of FIG. 1.
Figure 6:
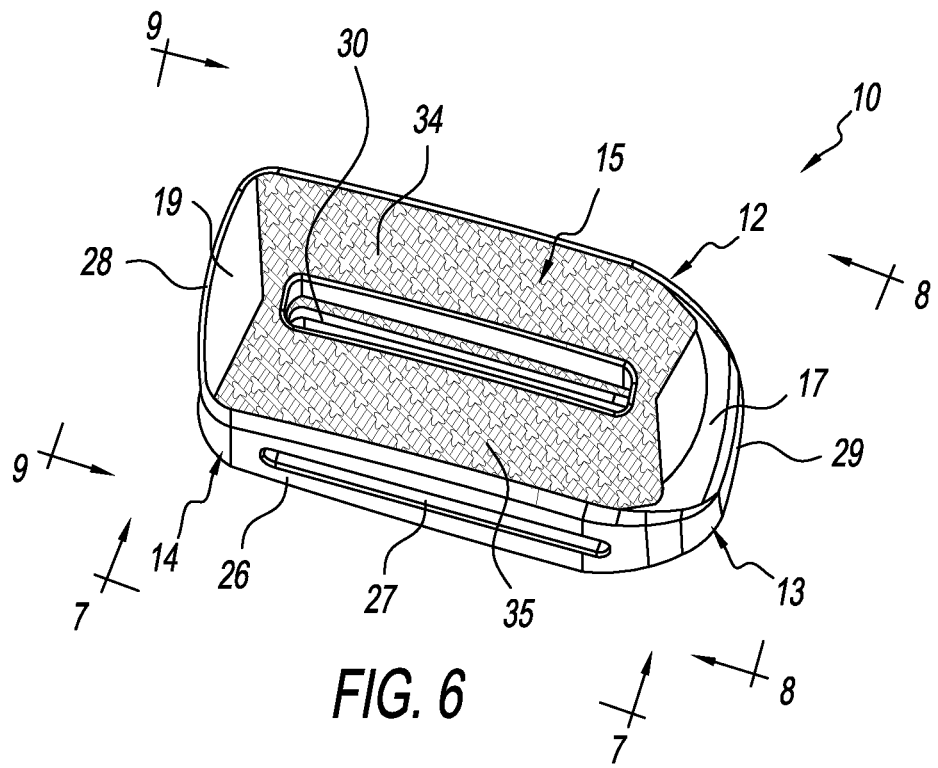
FIG. 6 is an isometric upper lateral side view of the 3-D printed spinal interbody implant of FIG. 1.

Referring to FIGS. 1-10, there is depicted an orthopedic implant fashioned as a spinal interbody device, cage, or implant, generally designated 10, 3-D printed in accordance with the principles of the present invention. The 3-D printed spinal interbody implant is shown as a T/PLIF cage, designed for posterior insertion into the spine. As indicated in the Summary of the Invention, various types of orthopedic implants such as spinal interbody implants may be generated by 3-D printing in accordance with the present principles, the spinal interbody implant 10 being only exemplary and representative of all of the various orthopedic and spinal interbody implants made in accordance with the present principles.

The 3-D printed spinal implant 10 has a solid or dense exterior structure, casing, shell, or the like 12 such as, but not limited to, that described in the Summary of the Invention, and a porous, permeable or the like (non-solid) interior structure 15 shown as a lattice, matrix, mesh, weave or the like, but which, without limitation, may be a honeycomb arrangement, simple cubic arrangement, tetrahedral arrangement, diamond arrangement, or the like. The exterior structure 12 is made from a biocompatible material such as, but not limited to, titanium, stainless steel, an alloy of titanium or stainless steel, PEEK, PET or PETE, or the like, that can be 3-D printed. The interior structure 15 is likewise made from a biocompatible material such as recited above, but also 3-D printed bone fusion or growth material, either natural, artificial, or a combination of natural and artificial. The bone fusion process is aided by 3-D printing bone fusion material as part or all of the interior structure 15. Bone fusion/growth material may be, and is contemplated to be, provided or introduced into the interior structure through one or more bone fusion material introduction structure(s) of the implant (e.g. bores 21, 22).

The exterior structure 12 defines a first end 14 and a second end 13, the nomenclature first and second being arbitrary here and throughout unless specified otherwise. The second end 13 is generally bullet shaped (other shapes and/or variations thereof may be used), while the first end 14 is generally broadly arched or arced (other shapes and/or variations thereof may be used). Because the exemplary spinal interbody implant 10 is designed for posterior insertion in the spine, the first, proximal, or posterior end 14 has various features to aid, help, allow, and/or permit the implant 10 to interact with one or more insertion/implantation instruments (not shown). In the implant as shown, the first end 14 has an upper endplate 18 and a lower endplate 19, each having a small curvature towards the arced rear 28 of the first end 14. The rear 28 has a central threaded bore 20 that is configured to receive an insertion tool or instrument (not shown), a first lateral bore 21 adjacent one side of the central bore 20, and a second lateral bore 22 adjacent the other side of the central bore. The first and second lateral bores 21, 22 are configured to allow receipt or introduction of bone growth/fusion material into the implant 10 and, particularly, into the interior matrix 15. The first end 14 is configured to support a portion of an upper (superior) vertebral body and a portion of a lower (inferior) vertebral body.

The second, distal, or anterior end 13 is configured and/or has features that aid, help, allow, and/or permit the nose 29 to penetrate the spinal cavity during insertion. In the implant as shown, the second end 13 has an upper endplate 16 and a lower endplate 17, each having a small curvature towards the nose 29, the nomenclature upper and lower being arbitrary, since the implant 10 is at least generally symmetric. The second end 13 is configured to support a portion of an upper (superior) vertebral body and a portion of a lower (inferior) vertebral body. Other configurations may be used.

The exterior shell 12 has a first slot, channel or the like 25 along a first lateral side 24 thereof such that the interior matrix 15 is exposed along the slot 25. The exterior shell 12 also has a second slot channel or the like 27 along a second lateral side 26 thereof such that the interior matrix 15 is exposed along the slot 27. The length of each slot 25, 27 may be shorter or longer than shown. For instance, the length of each slot 25, 27 may extend all the way to the nose 29. In one form (not shown), the slot is continuous from the first lateral side 24 to the second lateral side 26 (or vice versa) through the nose 29. Other configurations may be used.

Figure 7:
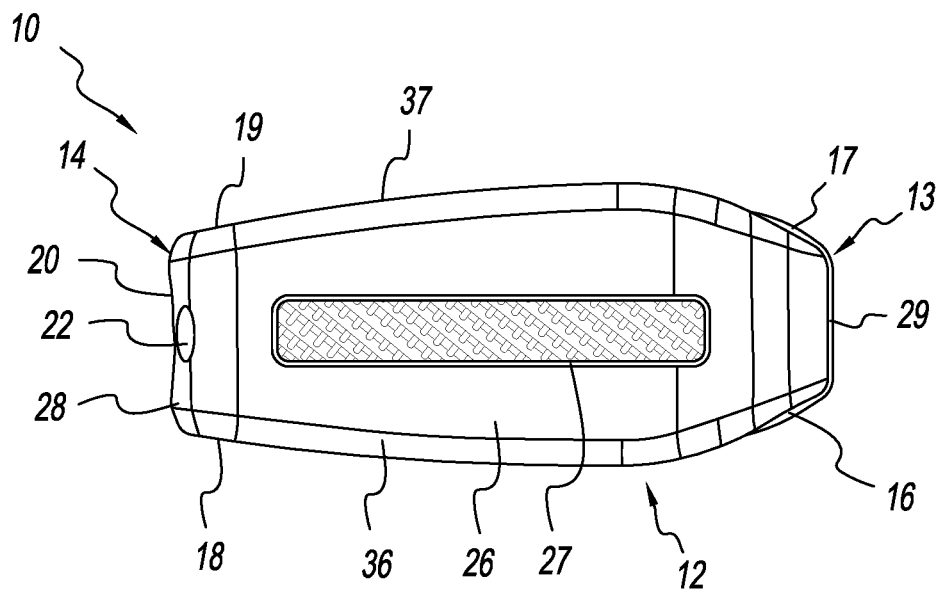
FIG. 7 is a lateral side plan view of the 3-D printed spinal interbody implant of FIG. 6 taken along line 7-7 thereof.
Figure 8:
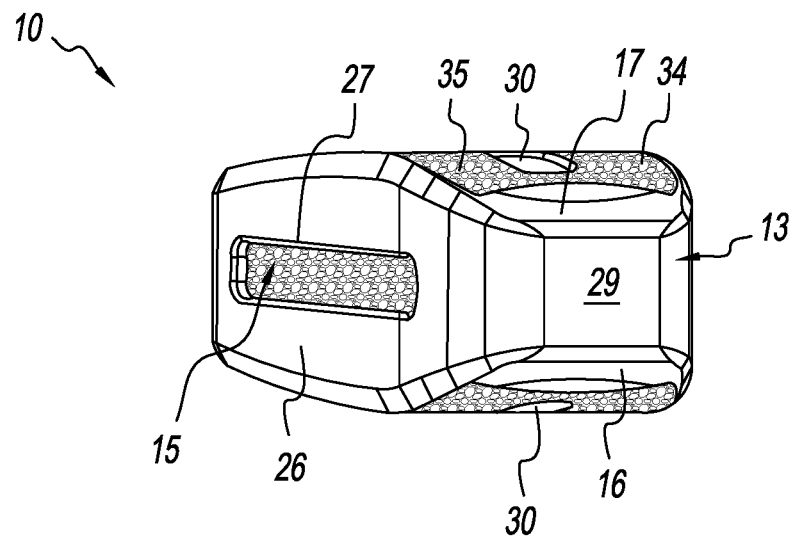
FIG. 8 is a lateral distal end view of the 3-D printed spinal interbody implant of FIG. 6 taken along line 8-8 thereof.
Figure 9:
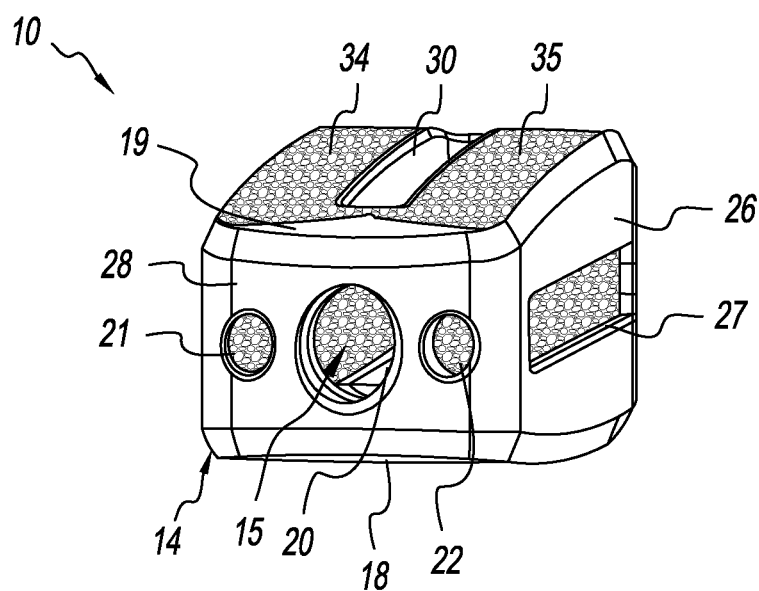
FIG. 9 is a lateral proximal end view of the 3-D printed spinal interbody implant of FIG. 6 taken along line 9-9 thereof.

The body 12 defines an upper (superior) surface 36 and a lower (inferior) surface 37 (see e.g. FIG. 7) but note that the body 12 is reversed in FIG. 7. Since the body 12 is generally symmetric, the upper surface may be the lower surface and vice versa. A cutout, void or the like 30 extends through the body 12 from the upper surface 37 to the lower surface 36 through the interior matrix 15. While the length of the cutout 30 is shown extending from adjacent the first end 14 to adjacent the second end 13, it may be of any length. As seen in the figures, the cutout 30 defines a first area or strip 32 of exposed interior matrix 15 along one side thereof along the upper surface 36, and a second area or strip 33 of exposed interior matrix 15 on another side thereof along the upper surface 36. Likewise, the cutout 30 defines a first area or strip 34 of exposed interior matrix 15 along one side thereof along the lower surface 37, and a second area or strip 35 of exposed interior matrix 15 on another side thereof along the lower surface 37. All of the interior structure that is exposed by the exterior structure provides areas for bone fusion.

Figure 10:
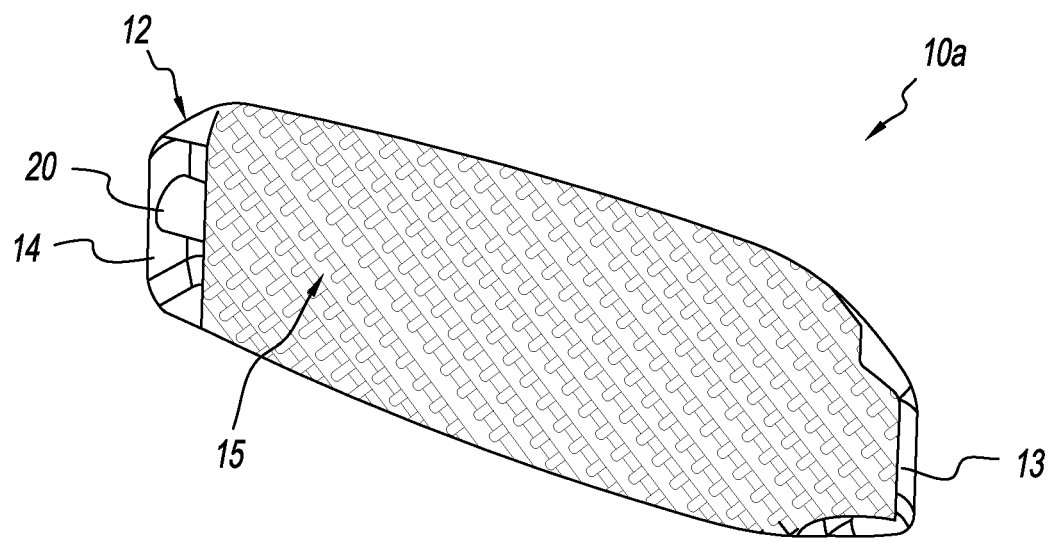
FIG. 10 is an isometric lower view of an upper portion of the 3-D printed spinal interbody implant of FIG. 1 particularly showing the interior structure.

FIG. 10 is a view of the interior structure 15 of a 3-D printed spinal interbody implant 10a via a cutaway view of a portion of the exterior structure 12 and a portion of the interior structure 15 thereof, the implant 10a similar to implant 10 without a central cutout 30, or a representation of the implant 10 before a central cutout 30 has been formed. In either case, the interior structure 15 may have an internal void or voids, or may be completely structure (without voids).

Figure 11:
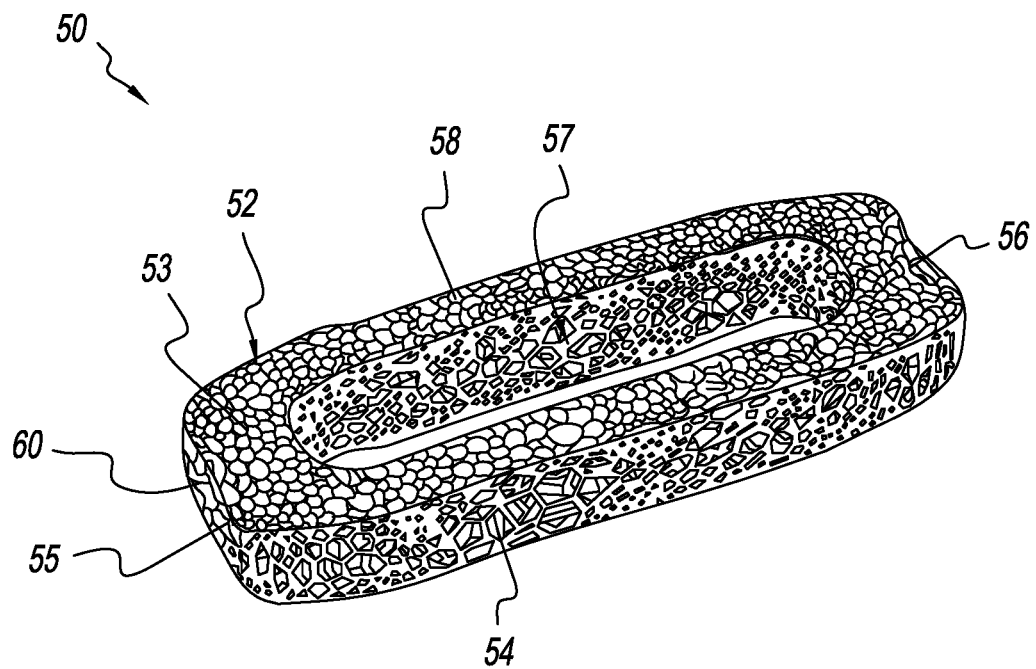
FIG. 11 is an isometric distal end view of another 3-D printed spinal interbody implant designed for intervertebral insertion.

FIG. 11 depicts a 3-D printed spinal interbody device generally designated 50 formed by a body 52 of an entirely porous, permeable or the like (non-solid) material shown as a variable sized open-celled structure, but may be, without limitation, a lattice, matrix, mesh, web, weave, honeycomb, simple cubic, tetrahedral, diamond, or the like such as described in the Summary of the Invention and/or shown and described herein. The body 52 is made from a biocompatible material such as, but not limited to, titanium, stainless steel, an alloy of titanium or stainless steel, PEEK, PET or PETE, or the like, that can be 3-D printed including bone fusion or growth material, either natural, artificial, or a combination of natural and artificial.

The body 52 defines an upper surface 53 and a lower surface (not seen in FIG. 11) opposite the upper surface 53, the nomenclature upper and lower being arbitrary. The body 52 further defines a first end 55 and a second end 56, as well as a first lateral side 54 and a second lateral side 58, the nomenclature first and second being arbitrary. The first end 55 is generally bullet shaped, while the second end 56 is generally arc-shaped. The first end 55 includes a bore 60 that is configured (via threading, no threading, or otherwise) to receive an insertion tool or instrument (not shown). The body 52 further has an opening 57 that extends from the upper surface 53 to the lower surface.

Figure 12:
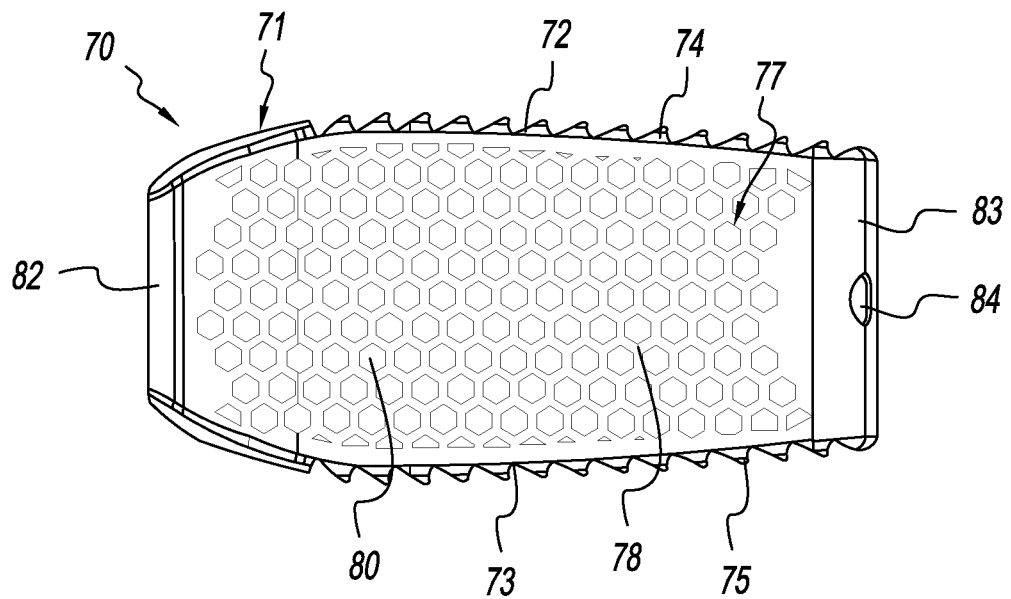
FIG. 12 is a side view of another 3-D printed spinal interbody implant designed for intervertebral insertion.
Figure 13:
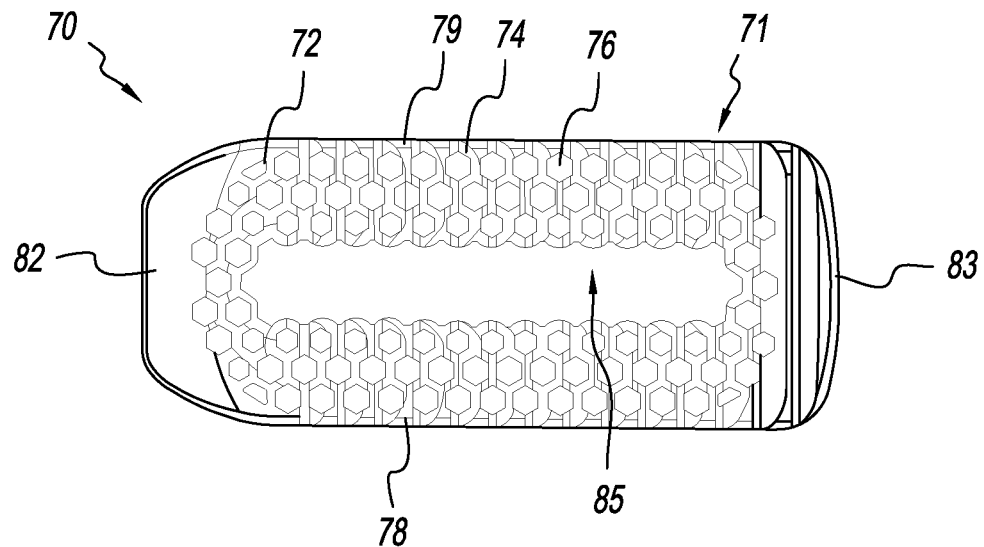
FIG. 13 is a top plan view of the 3-D printed spinal interbody implant of FIG. 12.

FIGS. 12 and 13 depict an orthopedic implant fashioned as a spinal interbody device, cage, or implant, generally designated 70, that is 3-D printed in accordance with the present principles. The 3-D printed spinal interbody implant 70 is shown as a T/PLIF cage, designed for posterior insertion into the spine.

The 3-D printed spinal implant 70 has a body 71 made from a biocompatible material such as, but not limited to, titanium, stainless steel, an alloy of titanium or stainless steel, PEEK, PET or PETE, or the like, that can be 3-D printed. Bone fusion/growth material may also be used. The body 71 defines an upper side 72 and a lower side 73, the nomenclature upper and lower being arbitrary, with a first lateral side 78 and a second lateral side 79. The body 71 also has a porous, permeable or the like (non-solid) middle section 77 formed as a plurality of hexagonal openings 80. A first end or nose 82 is defined at one end of the body 71 while a second end 83 is defined at the other end of the body 71, the nomenclature first and second being arbitrary. The first end 82 is formed of a solid or dense structure, the density of which may be the same throughout or variable as desired. The second end 83 is likewise formed of a solid or dense structure, the density of which may be the same throughout or variable as desired. A bore 84 is provided in the second end 83 which may or may not be threaded, in order to receive an insertion tool or instrument (not shown).

The upper side 72 includes a plurality of teeth, serrations or the like 74 that slant away from the first end 82. The lower side 73 likewise includes a plurality of teeth, serrations or the like 75 that also slant away from the first end 82. The teeth 74, 75 provide an anti-backout feature. A longitudinal opening 85 is formed in the middle section 77 between the first and second ends 82, 83 that extends from the upper side 72 to the lower side 73. Bone fusion/growth material may be, and is contemplated to be, provided or introduced into the interior structure via the longitudinal opening 85.

Figure 14:
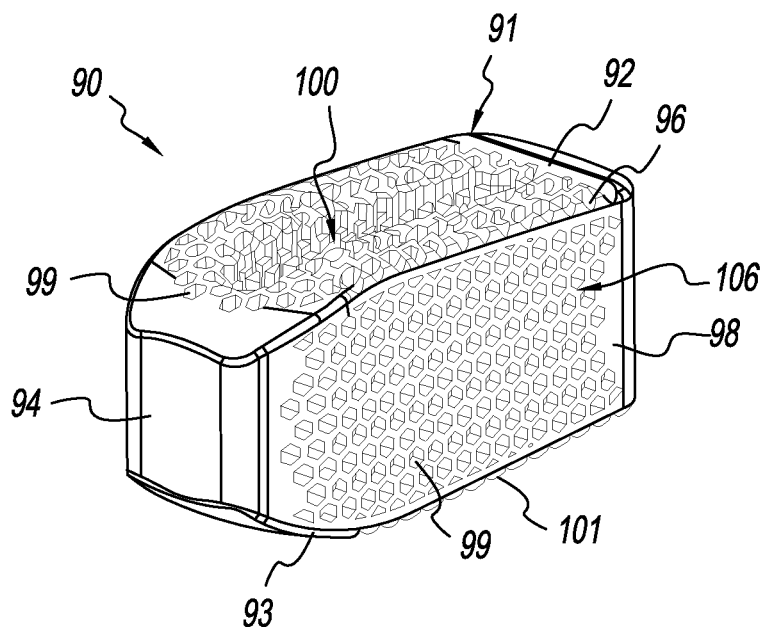
FIG. 14 is an isometric proximal end view of another 3-D printed spinal interbody implant designed for intervertebral insertion.
Figure 15:
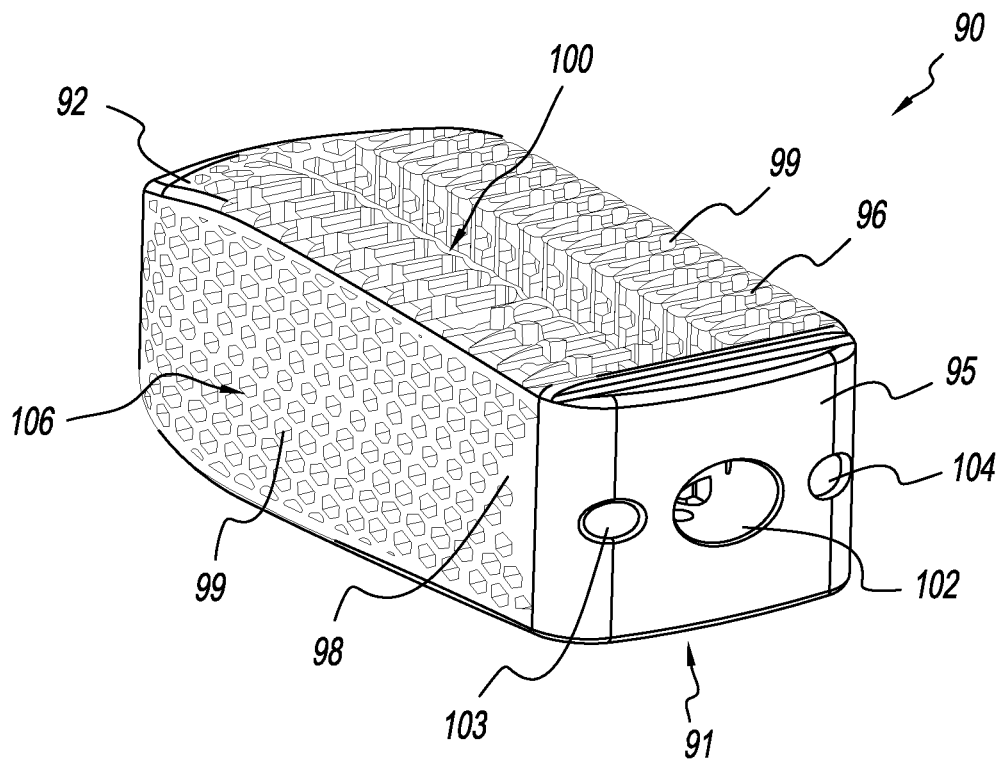
FIG. 15 is an isometric distal end view of the 3-D printed spinal interbody implant of FIG. 14.

FIGS. 14 and 15 depict another exemplary form of an orthopedic implant fashioned as a spinal interbody device, cage, or implant, generally designated 90, that is 3-D printed in accordance with the present principles. The 3-D printed spinal interbody implant 90 is shown as a T/PLIF cage, designed for posterior insertion into the spine.

The 3-D printed spinal implant 90 has a body 91 made from a biocompatible material such as, but not limited to, titanium, stainless steel, an alloy of titanium or stainless steel, PEEK, PET OR PETE, or the like, that can be 3-D printed. Bone fusion/growth material may also be used. The body 91 defines an upper side 92 and a lower side 93, the nomenclature upper and lower being arbitrary, with a first lateral side 98 and a second lateral side (not seen in the Figures). The body 91 also has a porous, permeable or the like (non-solid) middle section 106 formed as a plurality of hexagonal openings 99. A first end or nose 94 is defined at one end of the body 91 while a second end 95 is defined at the other end of the body 91, the nomenclature first and second being arbitrary. The first end 94 is formed of a solid or dense structure, the density of which may be the same throughout or variable as desired. The second end 95 is likewise formed of a solid or dense structure, the density of which may be the same throughout or variable as desired. A bore 102 is provided centrally in the second end 95 that is configured (via threading, no threading, or otherwise) to receive an insertion tool or instrument (not shown). A first lateral bore 103 is provided adjacent one side of the central bore 102, and a second lateral bore 104 is provided adjacent the other side of the central bore 102. The first and second lateral bores 103, 104 are configured to allow receipt or introduction of bone growth/fusion material into the interior of the implant 90.

The upper side 92 includes a plurality of teeth, serrations or the like 96 that slant away from the first end 94. The lower side 93 likewise includes a plurality of teeth, serrations or the like 101 that also slant away from the first end 94. The teeth 96, 101 provide an anti-backout feature. A longitudinal opening 100 is formed in the middle section 106 between the first and second ends 94, 95 that extends from the upper side 92 to the lower side 93. Bone fusion/growth material may be, and is contemplated to be, provided or introduced into the interior structure via the longitudinal opening 100.

Figure 16:
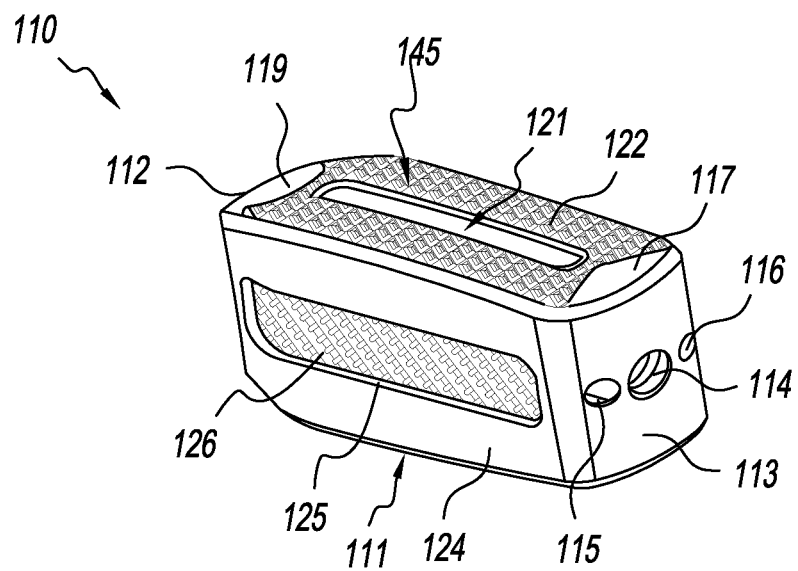
FIG. 16 is an isometric distal end view of another 3-D printed spinal interbody implant designed for intervertebral insertion.
Figure 17:
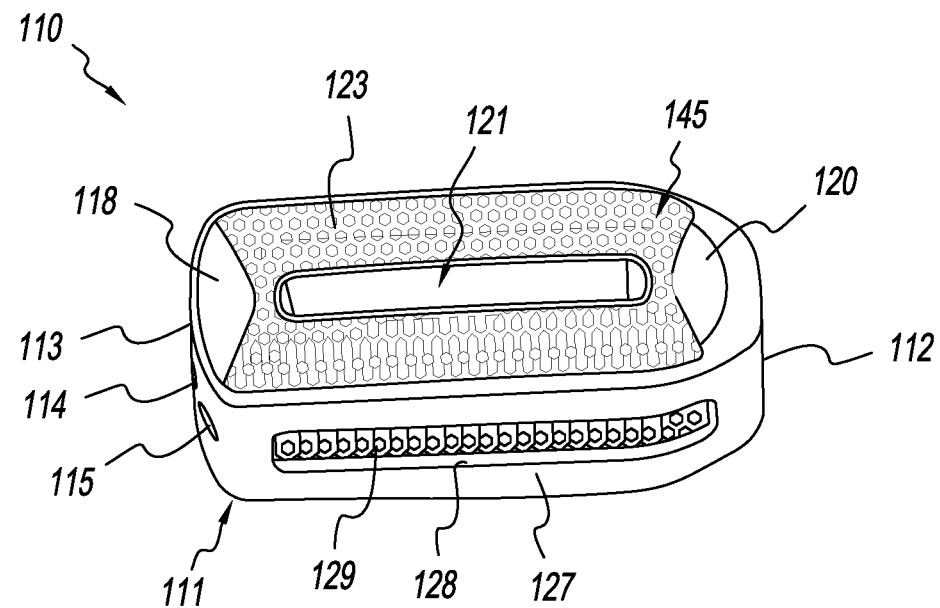
FIG. 17 is an isometric top lateral view of the 3-D printed spinal interbody implant of FIG. 16.

FIGS. 16 and 17 depict an orthopedic implant fashioned as a spinal interbody device, cage, or implant, generally designated 11, that is 3-D printed in accordance with the present principles. The 3-D printed spinal interbody implant 110 is shown as a T/PLIF cage, designed for posterior insertion into the spine.

The 3-D printed spinal implant 110 has a solid or dense exterior structure, casing, shell, or the like 111 such as, but not limited to, that described in the Summary of the Invention, and a porous, permeable or the like (non-solid) interior structure 145 shown as a mesh, but which, without limitation, may be a lattice, matrix, web, weave, honeycomb structure, simple cubic structure, tetrahedral structure, diamond structure, or the like such as, but not limited to, that described in the Summary of the Invention and/or shown and described herein. The exterior structure 111 is made from a biocompatible material such as, but not limited to, titanium, stainless steel, an alloy of titanium or stainless steel, PEEK, PET or PETE, or the like, that can be 3-D printed. The interior structure 145 is likewise made from a biocompatible material such as recited above, but also 3-D printed bone fusion or growth material, either natural, artificial, or a combination of natural and artificial. The bone fusion process is aided by 3-D printing bone fusion material as part or all of the interior structure 145. Bone fusion/growth material may be, and is contemplated to be, provided or introduced into the interior structure through one or more bone fusion material introduction structure(s) of the implant (e.g. bores 115, 116).

The exterior structure 111 defines a first end or nose 112 and a second end or rear 113, the nomenclature first and second being arbitrary here and throughout unless specified otherwise. The second end 113 is generally arc shaped, while the first end 112 is generally broadly arched or arced. Because the exemplary spinal interbody implant 110 is designed for posterior insertion in the spine, the second end 113 is a posterior end that has various features to aid, help, allow, and/or permit the implant 110 to interact with one or more insertion/implantation instruments (not shown). In particular, the second end 113 has an upper endplate 117 and a lower endplate 118. The second end 113 has a central threaded bore 114 that is configured to receive an insertion tool or instrument (not shown), a first lateral bore 115 adjacent one side of the central bore 114, and a second lateral bore 116 adjacent the other side of the central bore 114, the nomenclature first and second being arbitrary. The first and second lateral bores 115, 116 are configured to allow receipt or introduction of bone growth/fusion material into the implant 110 and, particularly, into the interior matrix 145. The second end 113 is configured to support a portion of an upper (superior) vertebral body and a portion of a lower (inferior) vertebral body.

The first end or nose 112 is an anterior end that is configured and/or has features that aid, help, allow, and/or permit the nose 112 to penetrate the spinal cavity during insertion. In particular, the first end 112 has an upper endplate 119 and a lower endplate 120, each having a small curvature towards the nose 112, the nomenclature upper and lower being arbitrary, since the implant 110 is at least generally symmetric. The first end 112 is configured to support a portion of an upper (superior) vertebral body and a portion of a lower (inferior) vertebral body. Other configurations may be used.

The exterior shell 111 has a first slot, channel or the like 125 along a first lateral side 124 thereof such that a portion 126 of the interior matrix 145 is exposed along the slot 125. The exterior shell 111 also has a second slot, channel or the like 128 along a second lateral side 127 thereof such that a portion 129 of the interior matrix 145 is exposed along the slot 128. The length of each slot 125, 128 may be shorter or longer than shown. For instance, the length of each slot 125, 128 may extend all the way to the nose 112.

The implant 110 defines an upper (superior) or top surface 122 and a lower (inferior) or bottom surface 123. Since the implant 110 is generally symmetric, the upper surface may be the lower surface and vice versa. A cutout, void, hole, or the like 121 extends through the implant 110 from the upper surface 122 to the lower surface 123 through the interior matrix 145. While the length of the cutout 121 is shown extending from adjacent the first end 112 to adjacent the second end 113, it may be of any length. As seen in the figures, the cutout 121 defines strips of exposed interior matrix 145 along its sides of the upper surface 122. Likewise, the cutout 121 defines strips of exposed interior matrix 145 along its side of the lower surface 123. All of the interior structure that is exposed by the exterior structure provides areas for bone fusion.

Figure 18:
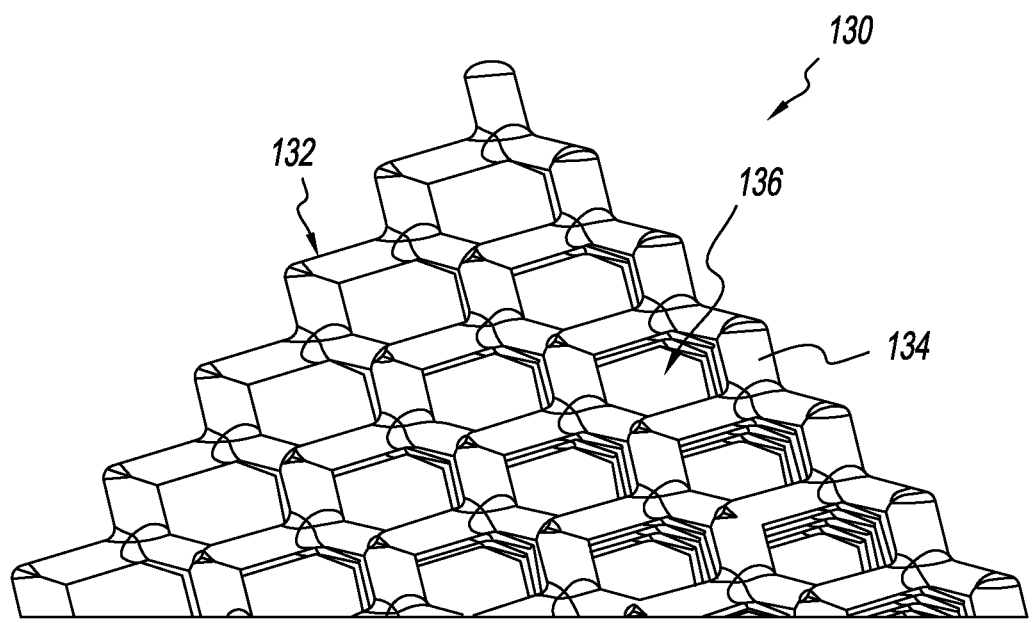
FIG. 18 is an isometric lateral view of an exemplary 3-D printed non-solid structure for use in the present spinal interbody implants.

Referring now to FIG. 18, there is depicted a 3-D printed porous, permeable, or non-solid structure or arrangement 130 that may be used for any or all portions of a 3-D printed orthopedic implant as taught herein. The structure/arrangement 130 is a diamond tetrahedral lattice 132. The lattice 132 may be of a single layer or multiple layers. The lattice 132 is composed of a plurality of linked hexagons 134 with open interiors 136. If multiple layers are used, each layer is stacked upon one another such that their openings 136 align. Other designs may be used.

Figure 19:
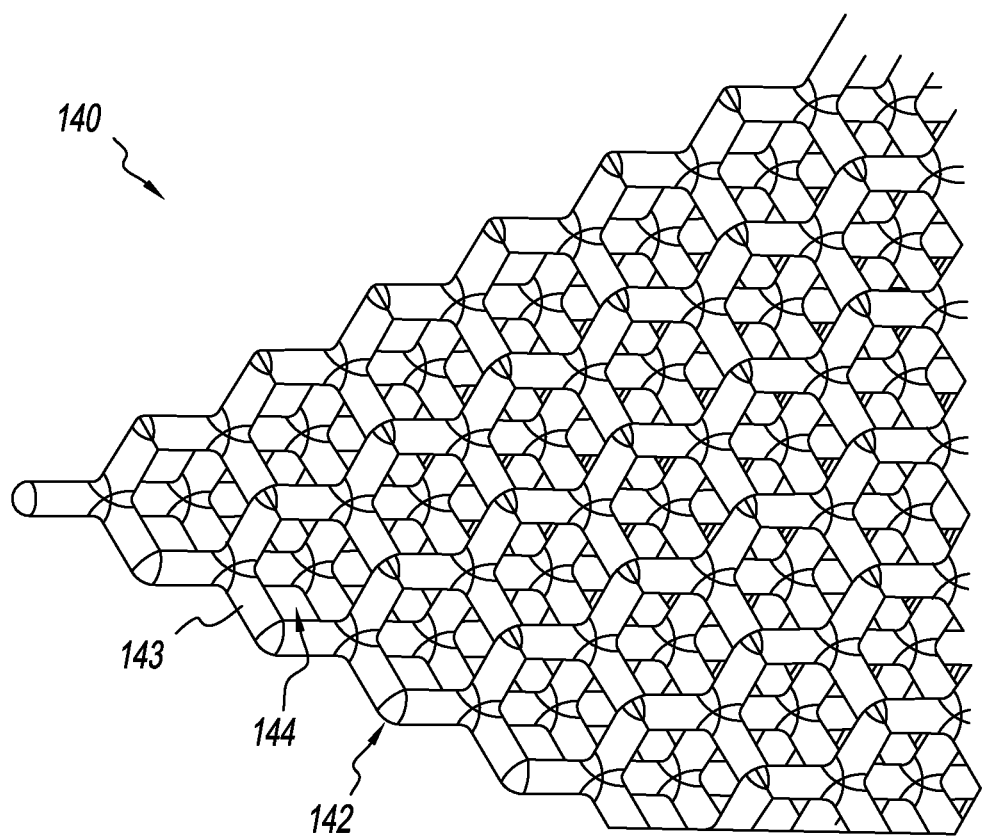
FIG. 19 is a top plan view of another 3-D non-solid structure for use in the present spinal interbody implants.
Figure 20:
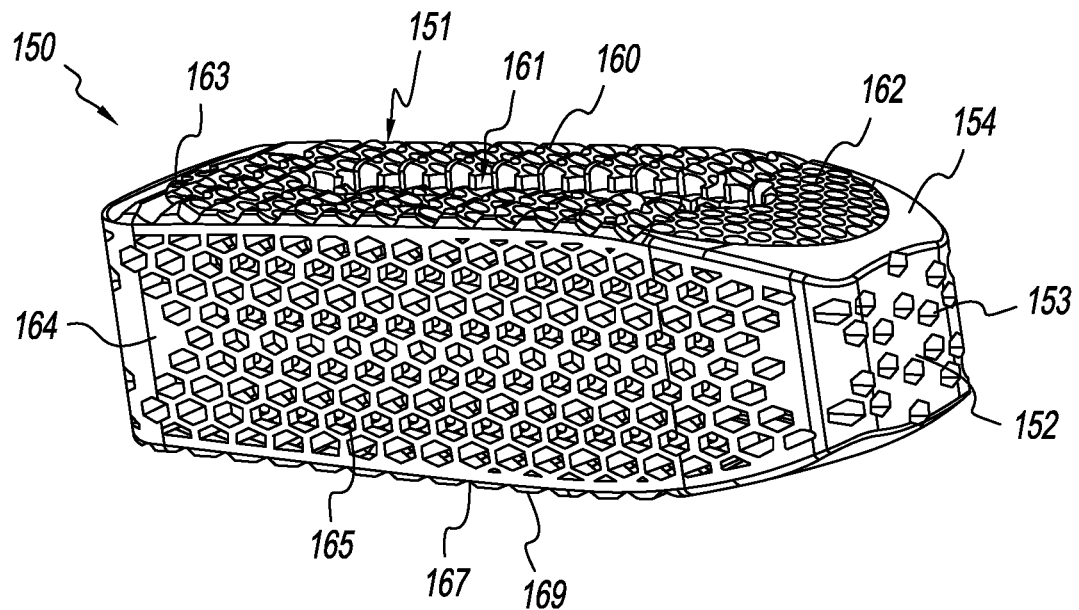
FIG. 20 is an isometric proximal lateral view of another 3-D printed spinal interbody implant designed for intervertebral insertion.
Figure 21:
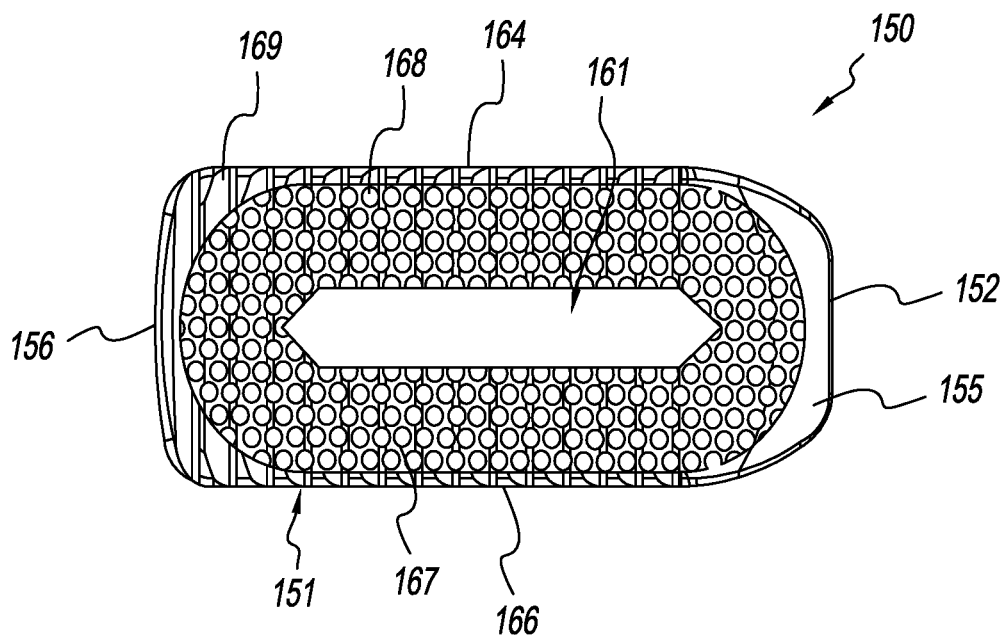
FIG. 21 is a top plan view of the 3-D printed spinal interbody implant of FIG. 20.
Figure 22:
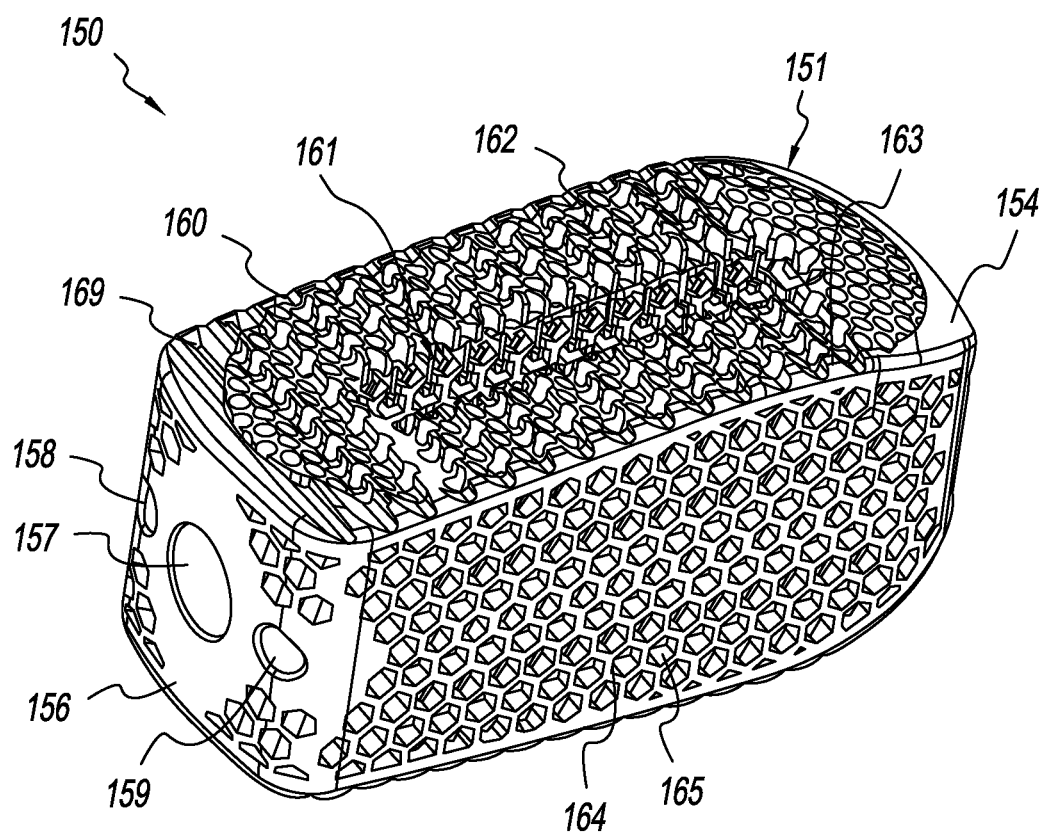
FIG. 22 is an isometric distal lateral view of the 3-D printed spinal interbody implant of FIG. 20.

Referring now to FIG. 19, there is depicted a 3-D printed porous, permeable, or non-solid structure or arrangement 140 that may be used for any or all portions of a 3-D printed orthopedic implant as described herein. The structure/arrangement 140 is an offset diamond tetrahedral lattice 142. The lattice 142 is composed of a plurality of linked hexagons 143 with open interiors 144. The lattice 142 has multiple layers stacked upon one another such that their openings 144 do not align. Other designs may be used.

Figure 23:
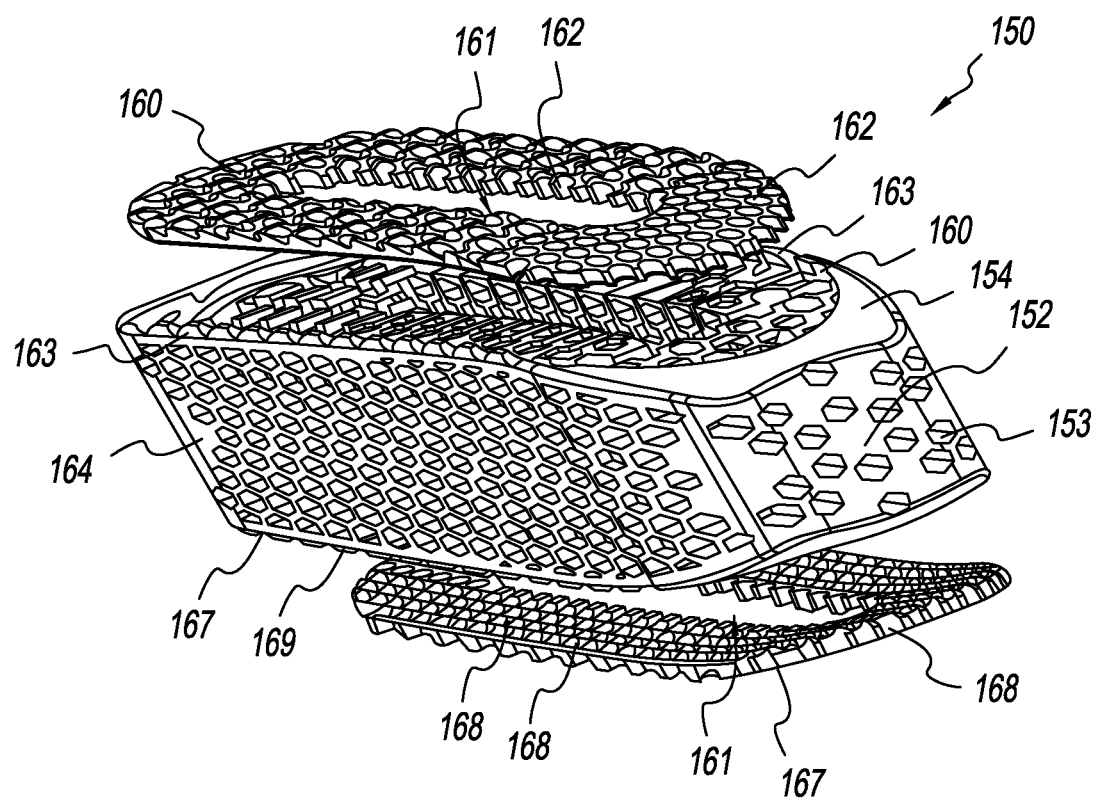
FIG. 23 is a proximal lateral view of the 3-D printed spinal interbody implant of FIG. 20 with portions thereof shown exploded from the body to illustrate their structure.
Figure 24:
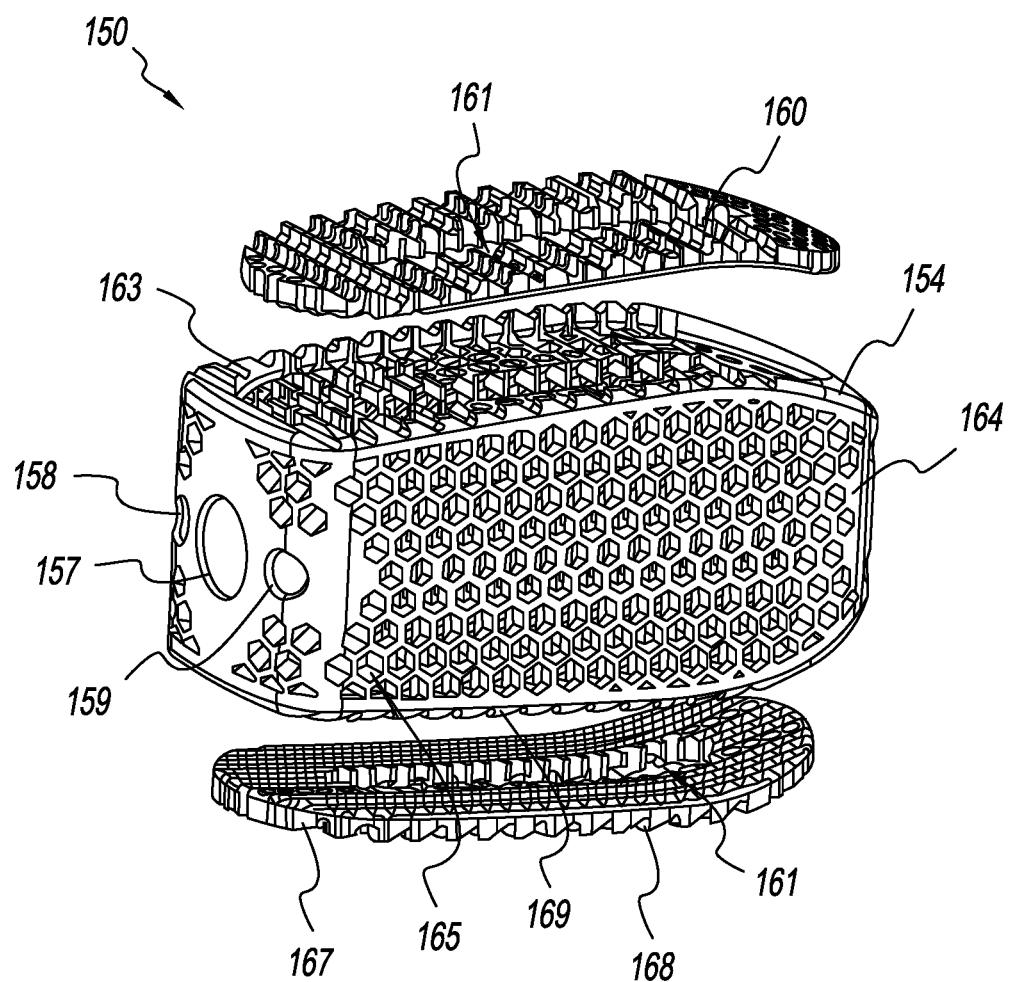
FIG. 24 is a distal lateral view of the 3-D printed spinal interbody implant of FIG. 20 with portions thereof shown exploded from the body to illustrate their structure.

FIGS. 20-24 depict a 3-D printed spinal interbody implant, device or cage generally designated 150. As described in greater detail below, the interbody implant 150 has a body 151 with a superior or upper endplate 160 and an inferior or lower endplate 167 each of which provides a contact surface for a superior or upper vertebral surface and for an inferior or lower vertebral surface. The endplates 160, 167 are 3-D printed as a highly porous or perforated mesh having a certain thickness such as, but not limited to, 0.25-3.0 mm. Of course, other thickness may be used. The highly porous mesh may have a pore size of 300-700 microns and, preferably, but not necessarily, 300-450 microns, but which may be greater than 700 microns or less than 300 microns, the pores 161 of the upper endplate 160, and the pores 168 of the lower endplate 167 are closely packed together with relatively thin (0.001-0.010 inch, but preferably, but not necessarily, 0.004-0.009 inch) walls in between with their axes generally perpendicular to the long axis of the implant. This pore size is thought to be most conductive to bone growth, by encouraging osteoblasts to enter the endplates through as large a surface area and as many individual pores as possible. The bulk of the remaining portions of the implant 150 has a porous structure with a pore size that is larger than the pore size of the endplates 160, 167 as well as thicker walls (e.g. 0.010-0.020 inch) in order to provide structural strength and also reduce radiodensity in preferred directions—i.e. in the direction of the hexagonal pores going from one sidewall of the implant to the other sidewall of the implant. FIGS. 23 and 24 show the upper porous endplate 164 and the lower porous endplate 167 in exploded view relative to the remainder of the less porous mesh of the implant 150 for clarity. It should be understood that the implant 150 is 3-D printed as a single piece and is not an assembly.

The implant is 3-D printed from a biocompatible material such as but not limited to, titanium, stainless steel, an alloy of titanium or stainless steel, PEEK, PET or PETE, or the like, including bone fusion or growth material, either natural, artificial, or a combination of natural and artificial. The bone fusion process is aided by the addition of bone fusion material into the interior of the implant 150.

The body 151 defines a first end or nose 152 and a second end or rear 156, the nomenclature first and second being arbitrary. Both the first end 152 and the second end 156 are generally arc shaped. Because the implant 150 is designed for posterior insertion in the spine, the second end 156 is a posterior end that has various features to aid, help, allow, and/or permit the implant 150 to interact with one or more insertion/implantation instruments (not shown). Particularly, the second end 156 a threaded bore 157 that is configured to receive an insertion tool, instrument or introducer (not shown), a first lateral bore 158 adjacent one side of the threaded bore 157, and a second lateral bore 159 adjacent the other side of the threaded bore 157, the nomenclature first and second being arbitrary. The first and second lateral bores 158, 159 are configured to allow receipt or introduction of bone growth/fusion material into the interior of the implant 150. The second end 156 is configured to support a portion of an upper (superior) vertebral body and a portion of a lower (inferior) vertebral body by having dense or solid portions at its upper side and lower side. Furthermore, the upper side of the second end 156 includes serrations or teeth 169 that aid in retention of the implant 150 in the intervertebral space. Likewise, the lower side of the second end 156 includes serrations or teeth (not shown) that aid in retention of the implant 150 in the intervertebral space.

The first end or nose 152 is an anterior end that is configured to penetrate the spinal cavity during insertion. The nose 152 has an upper endplate 154 and a lower endplate 155, each having a small curvature towards the nose 152, the nomenclature upper and lower being arbitrary.

The first end 152 is configured to support a portion of an upper (superior) vertebral body and a portion of a lower (inferior) vertebral body. Other configurations may be used. The nose 152 is generally porous as described above and thus includes a plurality of pores 153, each one shown as hexagonal in shape, but which may be other shapes if desired.

The implant 150 has a first lateral side or sidewall 164 having a plurality of hexagonal pores 165 and a second lateral side or sidewall 166 likewise having a plurality of hexagonal pores (not seen). The endplate 160 defines an upper (superior) or top surface, while the endplate 167 defines a lower (inferior) or bottom surface. Since the implant 150 is generally symmetric, the upper surface may be the lower surface and vice versa. A cutout, void, hole, or the like 161 extends through the implant 150 from the upper surface 160 to the lower surface 167 through the interior matrix of the implant 150. The length of the cutout 161 may vary from that shown.

A 3-D printed interbody spine implant per the principles of the present invention may be fashioned for a lateral insertion procedure, an anterior insertion procedure, a posterior insertion procedure or other, by varying the exterior structure and/or the interior structure of the implant body. Of course, variations in exterior structure provide various amounts of exposed interior structure.

With some, if not all, of the interbody implants shown and described herein, bone graft material (as set forth in the Summary of the Invention, above) is introduced into the implant post implantation through an aperture of the implant in order to promote fusion with the adjacent vertebrae. The method of delivering, injecting, or introducing bone graft material into the implant post-implantation can be accomplished before or after an introducer or implantation instrument (not shown), such as is known in the art, has been disengaged from the implant. The introducer instrument includes a bore for introducing the bone graft into the implant via an aperture of the implant.

Figure 25:
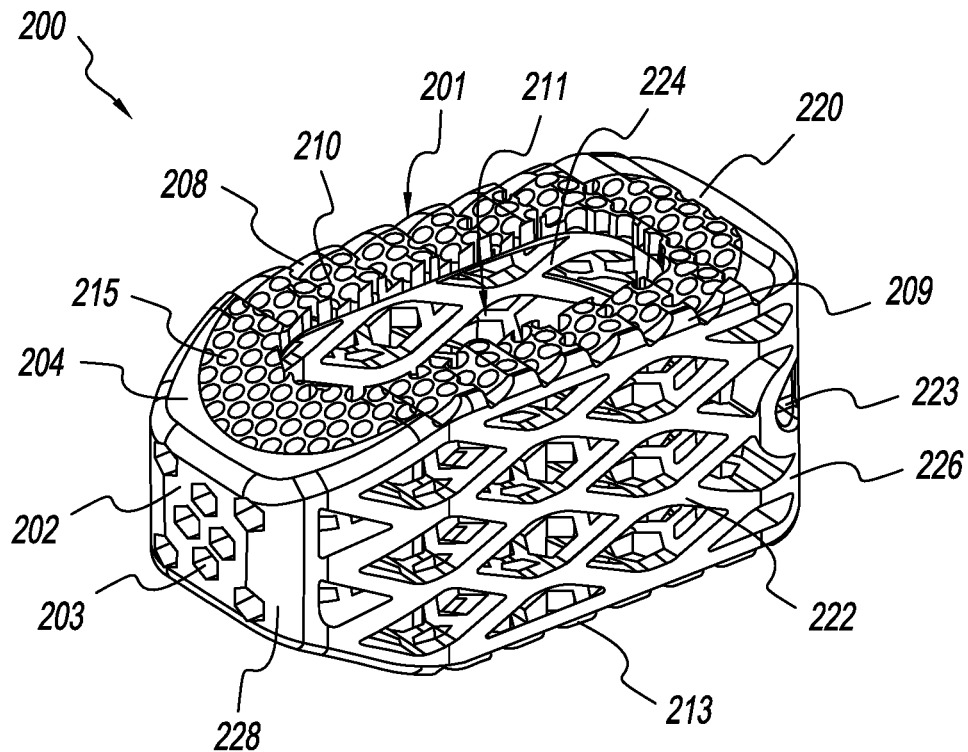
FIG. 25 is an isometric proximal end view of a 3-D printed orthopedic implant formed as a spinal interbody implant designed for posterior intervertebral insertion.
Figure 26:
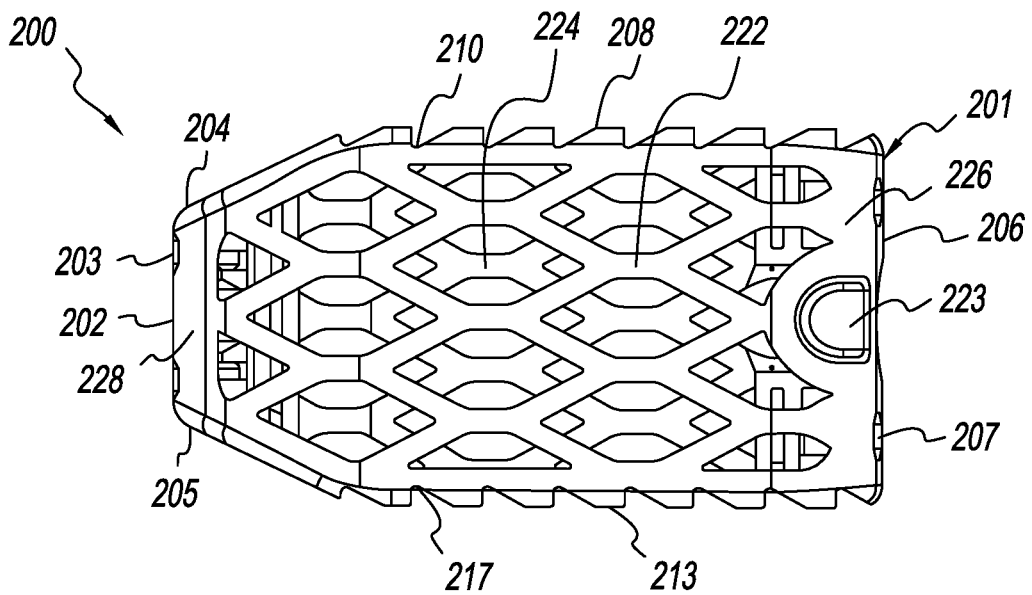
FIG. 26 is a side view of the 3-D printed spinal interbody implant of FIG. 25.
Figure 27:
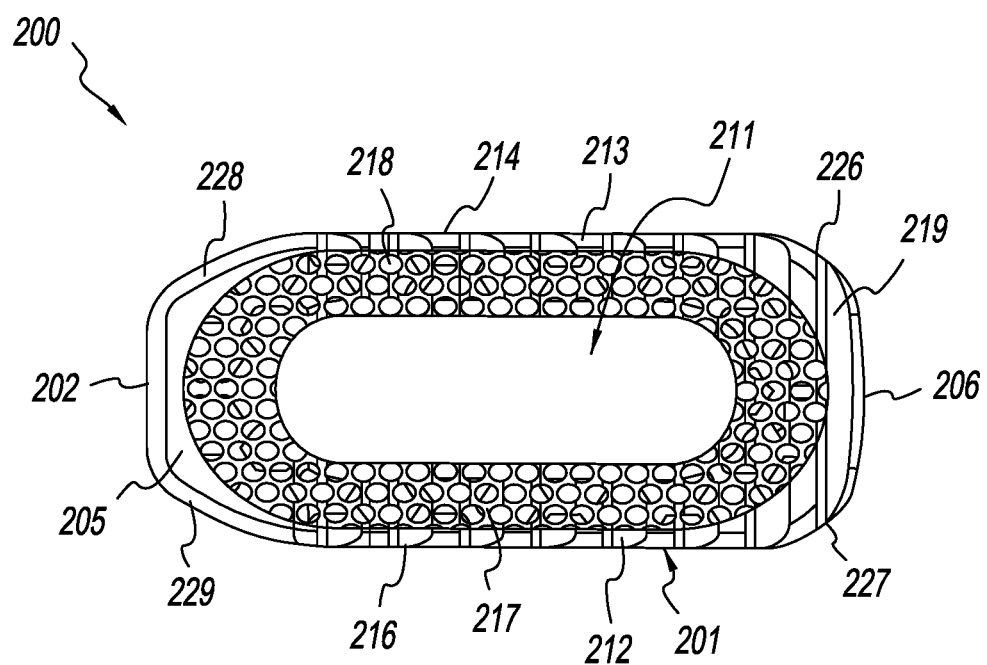
FIG. 27 is a bottom view of the 3-D printed spinal interbody implant of FIG. 25.

Referring to FIGS. 25-27, there is depicted a spine/spinal interbody implant, device, or cage generally designated 200 that is fabricated in accordance with the present principles using 3-D printing. The implant 200 is 3-D printed from a biocompatible material such as but not limited to, titanium, stainless steel, an alloy of titanium or stainless steel, PEEK, PET or PETE, other plastic, ceramic, or the like, including bone fusion or growth material, either natural, artificial, or a combination of natural and artificial.

The interbody implant 200 has a body 201 with a superior, upper or top (collectively, superior) side/surface 210 and an inferior, lower or bottom (collectively, inferior) side/surface 217 each of which provides a contact surface for a superior, upper or top vertebral surface (not shown) and for an inferior, lower or bottom vertebral surface (not shown). An opening 211 extends through the body 201 from the superior side/surface 210 to the inferior side/surface 217. The bone fusion process is aided by the addition of bone fusion material into the interior of the implant 200 via the opening 211.

The superior side/surface 210 is porous, providing communication with the interior of the implant 200, and thus has a plurality of holes 215 situated around the opening 211, the holes 215 closely spaced to one another. The plurality of holes 215 are preferably, but not necessarily, round or circular, but may be other shapes as desired. The inferior side/surface 217 is likewise porous, providing communication with the interior, and thus has a plurality of holes 218 situated around the opening 211, the holes 218 also closely spaced to one another. The plurality of holes 218 are preferably, but not necessarily, round or circular, but may be other shapes as desired. The plurality of holes 215, 218 provide pores into the interior of the implant 200 from the top to the bottom (superior to inferior) thereof such that the implant 200 is porous from top to bottom (superior to inferior). The plurality of holes 215, 218 have a first size that may be 300-700 microns and, preferably, but not necessarily, 300-450 microns, but which may be greater than 700 microns or less than 300 microns. This hole size is thought to be most conductive to bone growth, by encouraging osteoblasts to enter through as large a surface area and as many individual holes as possible. However, other sized holes may be used.

The superior side/surface 210 also has a first row of teeth, serrations or the like 208 situated along a first edge thereof, and a second row of teeth, serrations or the like 209 situated along a second edge thereof, the nomenclature first and second being arbitrary here and throughout. The inferior side/surface 217 also has a first row of teeth, serrations or the like 212 situated along a first edge thereof, and a second row of teeth, serrations or the like 213 situated along a second edge thereof. The teeth, serrations or the like aid in retention of the implant 200.

The body 201 also defines a first lateral side/surface 222 and a second lateral side/surface 224, the nomenclature first and second being arbitrary. The first lateral side/surface 222 is 3-D printed as a lattice having generally diamond shaped openings, although other shaped openings may be used. The second lateral side/surface 224 is also 3-D printed as a lattice having generally diamond shaped openings, although other shaped openings may be used. The plurality of diamond shaped openings provide large pores into the interior of the implant 200 from side to side (the first lateral side to the second lateral side) thereof such that the implant 200 is porous from side to side (the first lateral side to the second lateral side). The diamond shaped openings provide large porosity between the first and second lateral sides 222, 224. The diamond shaped openings of the lattice of the first and second sides/surfaces 222, 224 are preferably, but not necessarily larger than the size of the plurality of holes 215, 218 of the superior and inferior sides/surfaces 210, 217 (constituting a second porosity size).

The body 201 further defines a first end or nose 202 and a second end or rear 206. The nose 202 and rear 206 are each generally planar, although one or both may have curvature. The nose 202 transitions from the body 201 via a slanted superior surface 204, a slanted inferior surface 205, a first lateral curved surface 228, and a second lateral curved surface 229, each surface sans pores. The nose 202 has a plurality of hexagonally-shaped bores 203, although other shapes may be used. The plurality of hexagonal bores 203 either extend into the nose 202 but not into the interior, or into the interior if desired.

The rear 206 transitions from the body 201 via a generally planar superior surface 220, a generally planar inferior surface 219, a first curved lateral surface 226, and a second curved lateral surface 227. The first curved lateral surface 226 has a first cutout 223, and the second curved lateral surface 227 has a second cutout (not seen). The first and second cutouts 223, not seen, accept an installation instrument (not shown). The rear 206 has a plurality of hexagonally-shaped bores 207, although other shapes may be used. The plurality of hexagonal bores 203 either extend into the nose 202 but not into the interior, or into the interior if desired. The hexagonal bores 207 are preferably, but not necessarily, the same size as the hexagonal bores 203 of the nose 202. The spacing of the hexagonal bores 203 of the nose 202, of and the hexagonal bores 207 of the rear 206 are generally, but not necessarily, the same, and is greater, but not necessarily, than that of the superior and inferior sides/surfaces 210, 217.

The implant 200 thus has openings of different sizes and spacing about its body 201 providing porosity into the interior of the implant 200. While the body 201 of the implant 200 has three (3) different sizes of openings and spacing, there may be more or less of each—more or less differently sized openings and spacings may be used.

A 3-D printed interbody spine implant per the principles of the present invention may be fashioned for a lateral insertion procedure, an anterior insertion procedure, a posterior insertion procedure or other, by varying the exterior structure and/or the interior structure of the implant body. Of course, variations in exterior structure provide various amounts of exposed interior structure.

The method of delivering, injecting, or introducing bone graft material into the implant post-implantation can be accomplished before or after an introducer or implantation instrument (not shown), such as is known in the art, has been disengaged from the implant. The introducer instrument typically includes a bore for introducing the bone graft into the implant via an aperture of the implant.

It should be appreciated that dimensions of the components, structures, and/or features of the exemplary 3-D printed interbody spine implant may be altered as desired within the scope of the present disclosure. Moreover, the principles shown and described herein regarding spinal interbody implants are applicable to all 3-D printed orthopedic implants.

What is claimed is:

1. A 3-D printed orthopedic implant comprising:
an exterior structure including a first end, a second end opposite the first end, a first lateral side extending between the first and second ends, a second lateral side extending between the first and second ends and opposite the first lateral side, wherein the first lateral side comprises a first lattice of geometric openings extending into the cavity and the second lateral side comprises a second lattice of geometric openings extending into the cavity, wherein the first lattice of geometric openings does not align with the second lattice of geometric openings when viewed from the first lateral side, wherein the exterior structure comprises a first biocompatible material having a first density; and
an interior structure disposed within a central portion of the exterior structure, wherein the internal structure comprises a second biocompatible material having a second density that is less than the first density.

2. The 3-D printed orthopedic implant of claim 1, wherein the interior structure defines a cavity comprising an opening extending completely through the interior structure.

3. The 3-D printed orthopedic implant of claim 1, wherein the first lattice of geometric openings comprises a plurality of diamond shaped openings and the second lattice of geometric openings comprises a plurality of diamond shaped openings.

4. The 3-D printed orthopedic implant of claim 1, wherein the implant further includes a top surface and a bottom surface, wherein the top surface includes a plurality of porous openings and the bottom surface includes a plurality of porous openings, wherein the porous openings on the top surface and the bottom surface are smaller than the geometric openings on the first lateral side and the second lateral side.

5. The 3-D printed orthopedic implant of claim 4, wherein the porous openings on the top surface and the bottom surface are circular.

6. A 3-D printed spinal implant comprising:
a body having a superior surface, an inferior surface opposite the superior surface, a first end, a second end opposite the first end, a first lateral side extending between the first and second ends, and a second lateral side extending between the first and second ends, the second lateral side being opposite and substantially parallel to the first lateral side;
wherein the first lateral side includes a first plurality of openings extending into a cavity of the implant and a second plurality of openings extending into the cavity, wherein each of the openings of the first plurality of openings do not align with an opening of the second plurality of openings;
wherein the superior surface includes a third plurality of openings and the inferior surface includes a fourth plurality of openings, wherein the third plurality of openings and the fourth plurality of openings comprises a plurality of openings smaller than the first plurality of openings and the second plurality of openings; and
wherein the first end includes a fifth plurality of openings and the second end includes a sixth plurality of openings, wherein the fifth and sixth plurality of openings are larger than the third and fourth plurality of openings and smaller than the first and second plurality of openings.

7. The 3-D printed spinal implant of claim 6, wherein:
the body comprises one of titanium, stainless steel, an alloy of titanium or stainless steel, PEEK, and PET or PETE.

8. The 3-D printed spinal implant of claim 6, wherein the first plurality of openings and the second plurality of openings comprises a plurality of offset hexagonal openings.

9. A 3-D printed spinal implant comprising:
an exterior structure having a first end, a second end opposite the first end on the exterior structure, a first lateral side extending between the first and second ends, and a second lateral side extending between the first and second ends and opposite the first lateral side, the first lateral side and the second lateral side each having a lateral aperture disposed adjacent the first and second end, wherein the exterior structure comprises a first biocompatible material having a first density; and
an interior structure disposed within a central portion of the exterior structure, with a superior surface of the interior structure exposed on a top portion of the exterior structure and an inferior surface exposed on a bottom portion of the exterior structure, the interior structure comprising a second biocompatible material having a second density;
wherein the exterior structure includes a first plurality of openings proximate the first lateral side and a second plurality of openings proximate the second lateral side, wherein the first plurality of openings do not align with the second plurality of openings; and
wherein the first density of the first biocompatible material is greater than the second density of the second biocompatible material.

10. The 3-D printed spinal implant of claim 9, wherein:
the first plurality of openings and the second plurality of openings comprises one of a matrix, a lattice, or a mesh.

11. The 3-D printed spinal implant of claim 10, wherein:
the exterior structure comprises a non-porous material made of one of titanium, stainless steel, an alloy of titanium or stainless steel, PEEK, and PET or PETE; and
the interior structure comprises a porous material made of one of titanium, stainless steel, an alloy of titanium or stainless steel, PEEK, PET or PETE, and bone fusion/growth material.

12. The 3-D printed spinal implant of claim 11, wherein the bone fusion/growth material comprises one of a natural bone fusion/growth material, an artificial bone fusion/growth material, or a combination of natural fusion/growth material and artificial fusion/growth material.

13. The 3-D printed spinal implant of claim 9, wherein the first plurality of openings comprises a plurality of repeating polygon shaped openings.

14. A method of delivering bone graft material into a 3-D printed spinal implant, the method comprising:
implanting a 3-D printed spinal implant into a spine of a patient by using a cannulated introducer that has been connected to the 3-D printed spinal implant, wherein the 3-D printed spinal implant has a first plurality of repeating geometric openings in an outermost surface of a first lateral side, wherein each of the first plurality of repeating geometric openings extends into an interior cavity of the implant, and a second plurality of repeating geometric openings in an outermost surface of a second lateral side, wherein each of the second plurality of repeating openings extends into the interior cavity of the implant, wherein the first plurality of repeating geometric openings do not align with the second plurality of repeating geometric openings, and wherein the implant comprises an exterior structure comprising a first biocompatible material having a first density and an interior structure disposed within a central portion of the exterior structure comprising a second biocompatible material having a second density that is less than the first density; and
providing bone graft material into the interior cavity of the implanted 3-D printed spinal implant using the cannulated introducer while the cannulated introducer is still connected to the spinal implant.

15. The method of delivering bone graft material into a 3-D printed spinal implant of claim 14, wherein the first plurality of repeating geometric openings comprises a plurality of diamond shaped openings.

16. A method of delivering bone graft material into a 3-D printed spinal implant, the method comprising,
implanting a 3-D printed spinal implant into a spine of a patient using an introducer, the 3-D printed spinal implant having a cavity exposed via one or more apertures, a first lattice of geometric openings in an outer surface of a first lateral side, wherein each of the first lattice of geometric openings extends into the cavity of the implant, and a second lattice of geometric openings in an outer surface of a second lateral side, wherein each of the second lattice of geometric openings extends into the cavity of the implant, wherein the first lateral side is opposite and substantially parallel to the second lateral side, wherein the first lattice of geometric openings does not align with the second lattice of geometric openings, and wherein the implant comprises an exterior structure comprising a first biocompatible material having a first density and an interior structure disposed within a central portion of the exterior structure comprising a second biocompatible material having a second density that is less than the first density; and
introducing bone graft material into the cavity of the 3-D printed spinal implant by a bone graft material injector through the one or more apertures in the 3-D printed spinal implant.

17. The method of delivering bone graft material into a 3-D printed spinal implant of claim 16, wherein the first lattice of geometric openings comprises a plurality of offset hexagonal openings.

18. The method of delivering bone graft material into a 3-D printed spinal implant of claim 16, wherein introducing bone graft material into the cavity of the 3-D printed spinal implant by the bone graft material injector through the one or more apertures in the 3-D printed spinal implant is performed while the introducer is still connected to the spinal implant.

* * * * *